(12) United States Patent
Altemus

(10) Patent No.: US 7,207,328 B1
(45) Date of Patent: Apr. 24, 2007

(54) EMERGENCY AIR DELIVERY SYSTEM FOR PATIENTS

(76) Inventor: Armin Altemus, P.O. Box 55127, Riverside, CA (US) 92517-0127

( * ) Notice: Subject to any disclaimer, the term of this patent is extended or adjusted under 35 U.S.C. 154(b) by 413 days.

(21) Appl. No.: 10/629,409

(22) Filed: Jul. 29, 2003

(51) Int. Cl.
*A61M 16/00* (2006.01)

(52) U.S. Cl. .......................... 128/202.28; 128/205.13; 128/204.18

(58) Field of Classification Search ........... 128/200.11, 128/201.27, 201.28, 202.14, 202.27, 205.17, 128/202.28, 202.29, 203.11, 203.28, 203.29, 128/205.13, 205.14, 205.15, 205.16, 205.22, 128/206.12, 206.28; 2/102, 94, 95, 85; 224/148.2, 224/637, 639; 441/106–108
See application file for complete search history.

(56) References Cited

U.S. PATENT DOCUMENTS

| | | | | |
|---|---|---|---|---|
| 1,177,208 A | * | 3/1916 | Pierpont | ................. 128/202.28 |
| 1,197,232 A | * | 9/1916 | Pierpont | ................. 128/205.13 |
| 2,194,809 A | | 3/1940 | Powell, Jr. | |
| 3,536,071 A | * | 10/1970 | Ferrando | ................ 128/202.14 |
| 3,575,167 A | * | 4/1971 | Michielsen | ............ 128/205.28 |
| 3,820,348 A | * | 6/1974 | Fast | ............................ 405/186 |
| 4,183,247 A | | 1/1980 | Allen et al. | |
| 4,192,301 A | | 3/1980 | Hardwick | |
| 4,349,015 A | | 9/1982 | Alferness | |
| 4,752,263 A | * | 6/1988 | Pritchard et al. | ............. 114/88 |
| 4,870,962 A | * | 10/1989 | Sitnik | .................... 128/205.13 |
| 5,092,327 A | * | 3/1992 | Tragatschnig | .......... 128/205.13 |
| 5,249,890 A | * | 10/1993 | Bergstrom | .................. 405/186 |
| 5,787,880 A | | 8/1998 | Swanson et al. | |
| 6,796,744 B2 | * | 9/2004 | Jacoway et al. | ............ 405/186 |

* cited by examiner

*Primary Examiner*—Teena Mitchell
*Assistant Examiner*—Annette Dixon
(74) *Attorney, Agent, or Firm*—Knobbe, Martens, Olson & Bear, LLP

(57) ABSTRACT

As disclosed herein, the present invention relates to an improved respirator having a respirator mask, respirator bellows, respirator conduits, and mounting straps attached to the torso of an operator. The respirator mask is positioned over a patient's face so as to cover the nose and mouth. The respirator bellows are positioned under the arms of the operator and are attached to the mounting straps, which may be configured as a vest that can be worn by the operator. The respirator bellows communicate with the respirator mask via the respirator conduits. The operator can deliver air or oxygen to the respirator mask by pumping the respirator bellows with his or her arms. Advantageously, the pumping motion is actuated without the use of hands. The hands-free pumping action allows the operator to firmly secure the respirator mask in proper position on the patient's face with both hands.

14 Claims, 10 Drawing Sheets

EMERGENCY AIR DELIVERY SYSTEM FOR PATIENTS

BACKGROUND OF THE INVENTION

1. Field of the Invention

The present invention relates to medical equipment, and, in particular, concerns an emergency air delivery system for patients.

2. Description of the Related Art

As is generally known in the medical profession, Cardio-Pulmonary Resuscitation (CPR) often involves forced air respiration, which provides oxygen to a patient's lungs, in combination with chest compressions, which circulates oxygenated blood until an effective heartbeat and breathing can be restored in the patient. A typical CPR technique involves a two person team, wherein one person holds a respirator mask over the patient's mouth so as to provide air or oxygen to the patient while the second person leans over the patient's chest so as to perform chest compressions in a generally known manner.

Common respirator masks comprise a molded section having a cavity region that is adapted to cover the mouth and nose of a patient. Some types of respirator masks further comprise an upwardly extending tube section with a mouth piece that can be used by the operator to exhale air into the cavity region of the respirator mask via the mouth piece and the tube section to thereby deliver air to the mouth and nose of the patient. Unfortunately, exhaling spent air into the cavity region of the respirator mask, which typically comprises less oxygen than ambient air, may not provide a sufficient amount of oxygen to the patient. As a result, re-breathing spent air by the patient could be detrimental to the patient's health. Also, while administering respiration in this particular situation, the operator may quickly become fatigued from forcing air into patient's lungs using the operator's diaphragm to exhale air into the cavity region of the respirator mask.

Other types of respirator masks further comprise a respirator bag connected directly to the respirator mask, which can be actuated to provide external air or oxygen to the cavity region of the respirator mask. An operator provides air or oxygen to a patient by squeezing and releasing the respirator bag in a pumping manner.

Typically, one of the operator's hands holds the mask in position over the patient's mouth and nose while the operator's other hand actuates the pumping motion of the respirator bag. In some situations, respiration and chest compressions are alternately performed on the patient. For example, approximately fifteen chest compressions are administered followed by approximately two pumps of the respirator bag. This process can be repeated until the patient regains more normal respiratory and circulatory function.

Unfortunately, conventional respirator masks are quite large and, therefore, may be difficult to hold in proper alignment over the patient's mouth and nose with one hand. In some cases, air or oxygen leaks from the edges of the respirator mask where the respirator mask contacts the facial skin of the patient. Typically, operators with small hands may have difficulty applying enough pressure to the respirator mask to avoid air leakage. If air or oxygen is allowed to leak out, then the patient may not receive enough air or oxygen during forced respiration, which may adversely reduce the amount of oxygen administered to the patient's lungs resulting in less oxygen in the patient's blood stream. This unfortunate circumstance may rapidly deteriorate the patient's health.

From the foregoing, there currently exists a need for a manual respirator that is better secured to the patient's face so that air or oxygen has a reduced incident of leakage from the edges of the respirator mask. To this end, there is a need for a respirator that is better suited for use by individuals with smaller hands such that the mask can be more readily secured to the patient's face.

SUMMARY OF THE INVENTION

The aforementioned needs may be satisfied by a respiration system for providing compressed gas to a patient. In one embodiment, the system may comprise a mask adapted to cover the patient's nose and mouth and at least one bellows having an inner chamber and an input port and an output port connected thereto, wherein the at least one bellows is compressible by a user such that when being compressed, the at least one bellows exhausts gas out the inner chamber via the output port and wherein the bellows is resiliently expandable such that when the compression has ceased, the at least one bellows expands and draws gas into the inner chamber via the input port. The respiration system may further comprise at least one gas conduit interconnecting the output port of the at least one bellows to the mask such that compressed gas is conveyed to the patient via the at least one gas conduit and the mask in response to compression of the at least one bellows by the user and a harness attached to the at least one bellows, wherein the harness is sized so as to position the bellows adjacent the user's body such that the user can compress the at least one bellows without using their hands thereby freeing their hands to hold the mask so as to cover the patient's nose and mouth.

In one aspect, the respiration system may further comprise a gas source coupled to the input port, wherein the gas source comprises a source of compressed oxygen. In addition, the harness may be sized so as to maintain the at least one bellows in a position at a location where the user can compress the at least one bellows between their inner upper arm and torso. The harness may also be sized so as to maintain the at least one bellows immediately adjacent the user's arm pit. The harness may further comprise at least one shoulder strap that rests on at least one shoulder of the operator so as to support the at least one bellows when the at least one bellows is positioned between the inner upper arm and the torso of the operator.

In another aspect, the respiration system may comprise two bellows, wherein the harness is sized so as to maintain the two bellows in a position at a location where the user can compress the two bellows between their inner upper arms and torso. In addition, the harness may be sized so as to maintain the at least one bellows immediately adjacent the user's right and left arm pit. Also, the harness may comprise a front strap connected between the two bellows across the front portion of the operator's torso and a rear strap connected between the two bellows across the rear portion of the operator's torso, and wherein the front strap comprises a locking device that is detachable and reattachable so as to allow the operator to remove the harness. Furthermore, the locking device may be selected from the group consisting of a hook and loop clasp, a button, a snap, a hook, and a buckle.

In another embodiment, the aforementioned needs may also be satisfied by a respirator for a patient administered by an operator, wherein the respirator may comprise a mask adapted to cover at least a portion of the patient's face, and at least one conduit attached to the mask so as to communicate with the mask. The respirator may further comprise at least one bellow adapted to be positioned between an arm and torso of the operator and attached to the at least one conduit so as to communicate with the conduit, wherein the at least one bellow can be compressed with a downward motion of the arm towards the torso of the operator so as to force gas from the bellow into the mask via the at least one conduit and decompressed with an upward motion of the arm away from the torso of the operator so as to draw gas into the bellow, and wherein the hands-free actuation of the at least one bellow allows the operator to secure the mask to the patient's face with more than one hand.

In one aspect, the mask may comprise a retaining edge that contacts the facial skin of the patient, wherein the hands-free actuation of the bellow allows the operator to firmly press the retaining edge against the facial skin of the patient to thereby reduce gas leakage from the mask during compression of the bellow. Additionally, the conduit may comprise flexible tubing such that the conduit communicates with the mask via a coupling device, wherein the coupling device directs gas, which may comprise at least one of air or oxygen, flowing through the conduit into the mask. Also, the at least one bellow may comprise a bag or sack with a inner closed cavity, wherein the bag or sack is formed of resilient material that can be squeezed into compression so as to force gas from the inner closed cavity and released for decompression so as to draw gas into the inner closed cavity.

In still another embodiment, the aforementioned needs may also be satisfied by an air delivery system for a patient administered by an operator, wherein the air delivery system may comprise a mask adapted to cover at least a portion of the patient's face, a harness attached to the torso of the operator, and a first bellow attached to the harness such that the first bellow is adapted to be positioned between the operator's right arm and torso, the first bellow having a first conduit attached to the mask so as to communicate therewith, wherein the first bellow can be compressed with a downward motion of the operator's right arm towards the operator's torso so as to force gas from the first bellow into the mask via the first conduit, and wherein compression of the first bellow allows the operator to secure the mask to the patient's face with the operator's right hand. Additionally, the air delivery system may further comprise a second bellow positioned between the operator's left arm and torso, the second bellow having a second conduit attached to the mask so as to communicate therewith, wherein the second bellow can be compressed with a downward motion of the operator's left arm towards the operator's torso so as to force gas from the second bellow into the mask via the second conduit, and wherein compression of the second bellow allows the operator to secure the mask to the patient's face with the operator's left hand.

In one aspect, the first and second bellows can be independently or simultaneously compressed. The first bellow can be decompressed with an upward motion of the right arm away from the torso of the operator so as to draw gas into the first bellow. The second bellow can be decompressed with an upward motion of the left arm away from the torso of the operator so as to draw gas into the second bellow. The first and second bellows can be independently or simultaneously decompressed.

In addition, the system may further comprise a harness that is adapted to be secured to the operator's torso, wherein the harness may comprise a right shoulder strap that rests on the operator's right shoulder, a left shoulder strap that rests on the operator's left shoulder, a front strap that crosses the operator's chest, and a rear strap that crosses the operator's back. The first bellow may be attached to the right shoulder strap of the harness and the second bellow is attached to the left shoulder strap of the harness. The front strap of the harness may comprise a locking device that is detachable and re-attachable so as to allow the operator to wear the harness, wherein the locking device may be selected from the group consisting of a hook and loop clasp, a button, a snap, a hook, and a buckle.

In yet another embodiment, the aforementioned needs may be satisfied by a method for providing compressed gas to a patient by an operator. The method may comprise covering the patient's nose and mouth with a respirator mask, securing the respirator mask to the patient's face with at least one of the operator's hands, and attaching a harness having at least one bellow to an operator's torso so that the at least one bellow is positioned between at least one of the operator's arms and torso. The method may further comprise attaching at least one conduit between the at least one bellow and the mask so that the at least one bellow communicates with the mask via the at least one conduit, compressing the bellow with at least one of the operator's arms against the operator's torso so as to force air through the conduit into the mask, and releasing the operator's arm from the bellow and the torso so as to allow decompression of the bellow to thereby draw gas into the bellow. These and other objects and advantages of the present invention will become more fully apparent from the following description taken in conjunction with the accompanying drawings.

DETAILED DESCRIPTION OF THE PREFERRED EMBODIMENT

Reference will now be made to the drawings, wherein like numerals refer to like parts throughout. An improved respirator capable of administering efficient air or oxygen delivery to a patient will be described in greater detail herein below with reference to the drawings.

Figure 1:
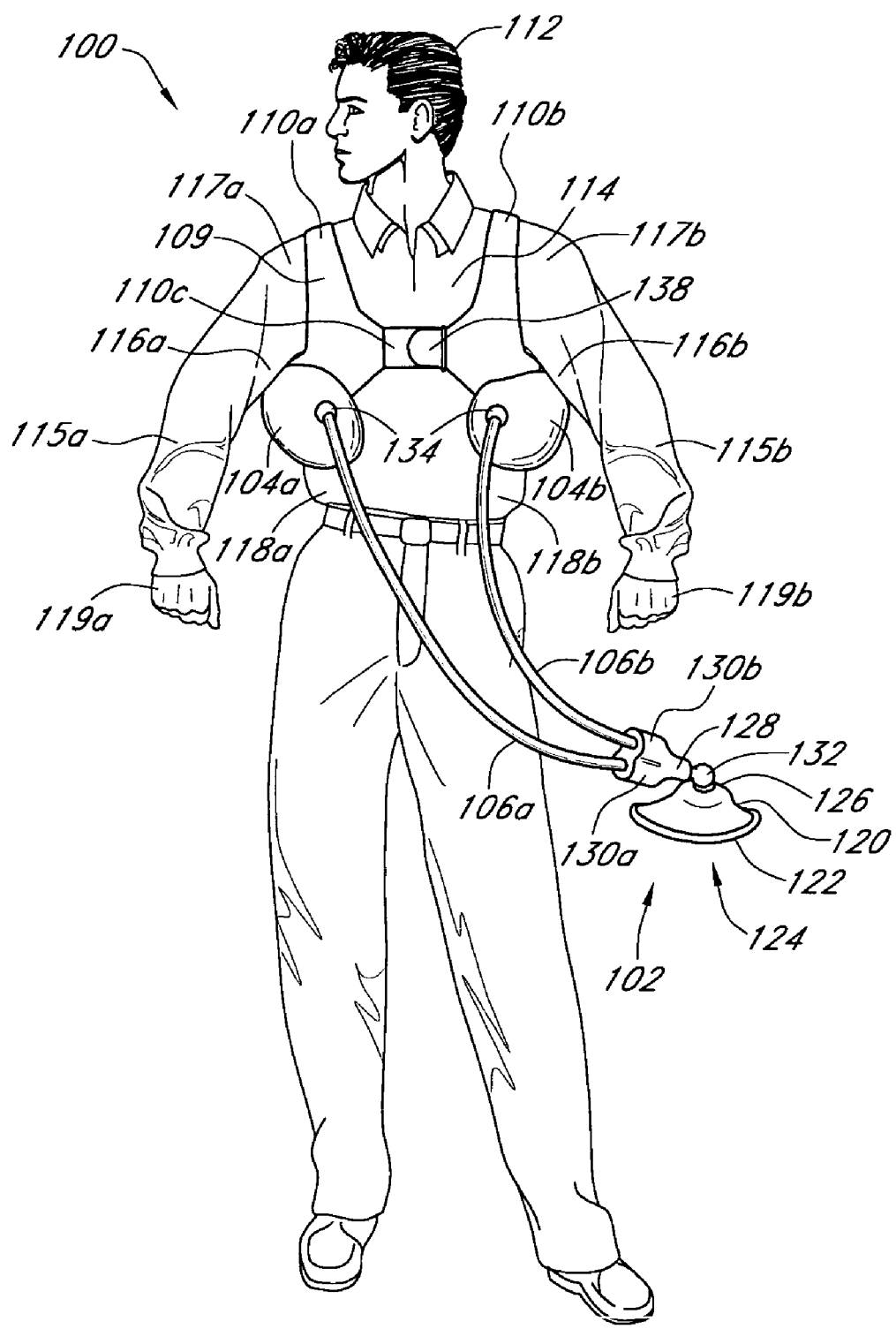
FIG. 1 illustrates a front view of one embodiment of an improved respirator having a respirator mask, one or more respirator bellows, one or more respirator conduits, and a respirator harness having mounting straps attached to an torso of an operator.
Figure 2:
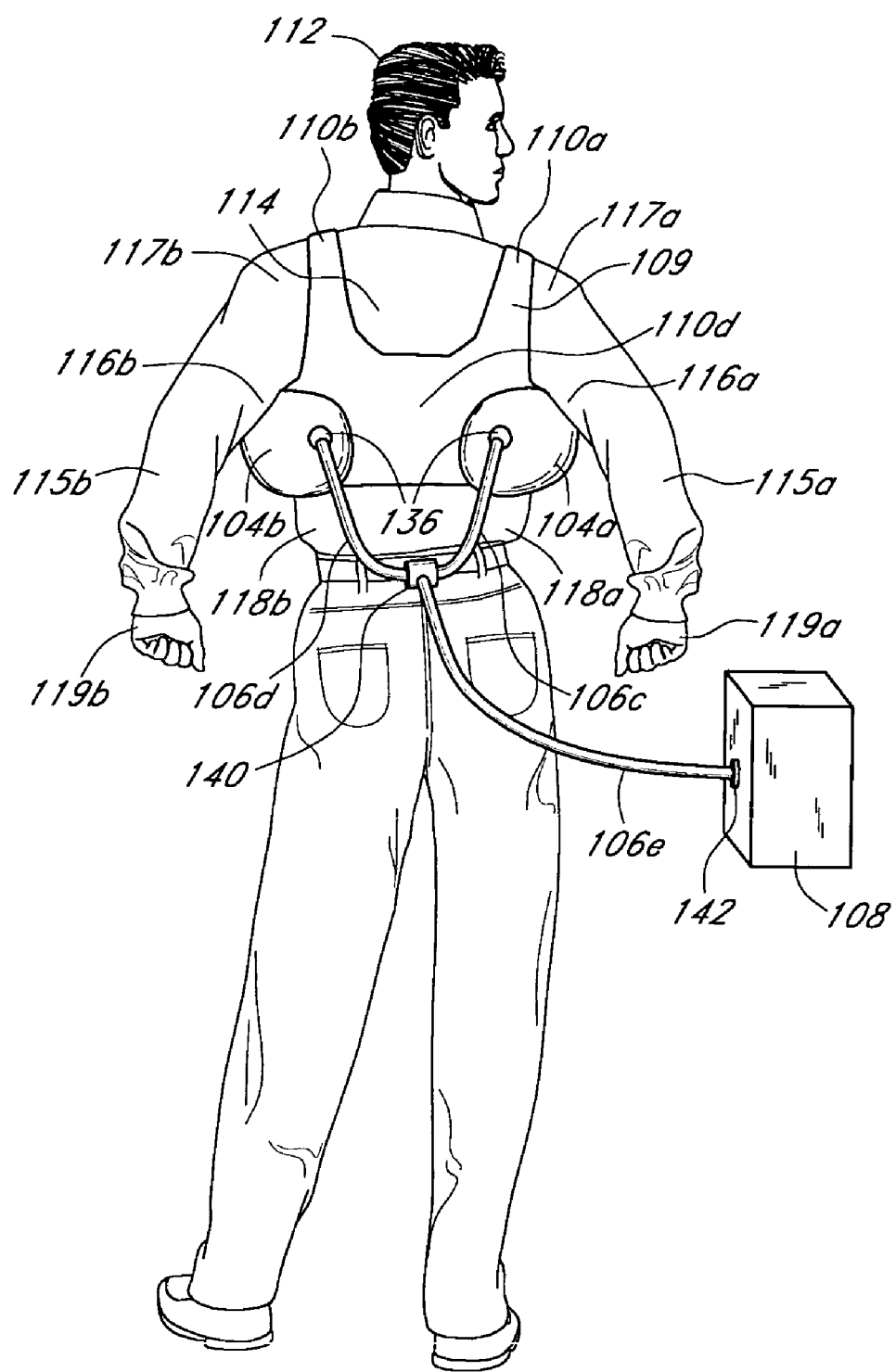
FIG. 2 illustrates a rear view of the improved respirator attached to the torso of the operator with the mounting harness, wherein an air or oxygen supply device may be attached to the one or more respirator bellows via additional respirator conduits.

FIG. 1 illustrates a front view of one embodiment of an improved respirator 100 having a respirator mask 102, respirator bellows 104a, 104b, respirator conduits 106a, 106b, and a respirator harness 109 attached to a torso 114 of an operator 112 having right and left arms 115a, 115b, right and left shoulders 117a, 117b, and right and left hands 119a, 119b, respectively. FIG. 2 illustrates a rear view of the improved respirator 100 attached to the torso 114 of the operator 112, wherein an air or oxygen supply device 108 may be attached to the respirator bellows 104a, 104b via additional respirator conduits 106c, 106d, 106e. As illustrated in FIGS. 1, 2, the torso 114 of the operator 112 has right and left side portions 118a, 118b, and the right and left arms 115a, 115b of the operator 112 have inner upper arms 116a, 116b, respectively. It should be appreciated that the inner upper arms 116a, 116b may also be referred to as inner arm pit portions of the right and left arms 115a, 115b.

As further illustrated in FIGS. 1, 2, the respirator harness 109 may comprise one or more mounting straps 110a, 110b, 110c, 110d, wherein the respirator bellows 104a, 104b are secured to the respirator harness 109 via the one or more mounting straps 110a, 110b, 110c, 110d. The scope and functionality of the respirator harness 109 including the mounting straps 110a, 110b, 110c, 110d will be described in greater detail herein below. In addition, the right and left hands 119a, 119b of the operator 112 may be gloved with generally known sanitary gloves so as to protect the operator 112 and the patient (shown in FIGS. 4A–4E) from cross-contamination without departing from the scope of the present invention.

In one embodiment, the respirator mask 102 comprises a facial cup 120 having a retaining edge 122 that contacts the facial skin of the patient in a manner as will be shown in FIG. 4. The facial cup 120 of the respirator mask 102 comprises an open-ended cavity 124 that is adapted to simultaneously cover at least one of the mouth and nose of a patient such that air or oxygen can be administered to at least one of the nose and mouth of the patient via the open-ended cavity 124 of the facial cup 120. The respirator mask 102 further comprises an input port 126 that is positioned adjacent the upper portion of the facial cup 120, which is substantially opposite the open-ended cavity 124. In addition, the input port 126 comprises a circular opening in the upper sidewall of the respirator mask 102 to thereby serve as a passageway for air or oxygen to flow through and into the facial cup 120.

Moreover, the respirator mask 102 further comprises a coupler 128 that joins at least one distal end of the respirator conduits 106a, 106b to the facial cup 120 via the input port 126. As illustrated in FIG. 1, the coupler 128, in one embodiment, comprises a first and second channel 130a, 130b that are each open at one distal end and are integrally formed together at a base channel 132 so that air or oxygen that is flowing separately into each channel 130a, 130b of the coupler 128 is added together in the base channel 132 and directed to the facial cup 120 via the input port 126. Advantageously, the additive force of the directed air or oxygen provides more air or oxygen to the patient such that more efficient respiration occurs, wherein an increased amount of air or oxygen can be delivered to the respirator mask 102 and a patient with more than one respirator conduit 106a, 106b. It should be appreciated by one skilled in the art that the respirator mask 102 may comprise a mouth piece, an endotracheal tube, or the like without departing from the scope of the present invention.

In one embodiment, the respirator bellows 104a, 104b may be positioned between the inner upper portions 116a, 116b of the arms 115a, 115b and the side portions 118a, 118b of the torso 114 of the operator 112 and secured to the torso 114 of the operator 112 with the mounting straps 110a, 110b, 110c, 110d of the respirator harness 109. As illustrated in FIGS. 1, 2, a first respirator bellow 104a may be positioned between the inner arm pit portion 116a of the right arm 115a and the right side portion 118a of the torso 114 of the operator 112, and a second respirator bellow 104b may be positioned between the inner arm pit portion 116b of the left arm 115b and the left side portion 118b of the torso 114 of the operator 112. The scope and functionality of the respirator bellows 104a, 104b will be described in greater detail herein below with reference to FIGS. 3A–4.

It should be appreciated by one skilled in the art that the improved respirator 100 as described herein may comprise a single respirator bellow, either the first or second respirator bellow 104a, 104b, positioned between at least one of the inner upper portions 116a, 116b of at least one of the arms 115a, 115b and at least one of the side portions 118a, 118b of the torso 114 of the operator 112 without departing from the scope of the present invention.

In one embodiment, the respirator harness 109 comprises a right shoulder mounting strap 110a, a left shoulder mounting strap 110b, a front mounting strap 110c, and a rear mounting strap 110d. In addition, the mounting straps 110a, 110b, 110c, 110d may comprise flexible, resilient material, such as nylon. As illustrated in FIGS. 1, 2, the right shoulder mounting strap 110a is attached to the first respirator bellow 104a so as to define an opening that receives the right arm 115a there through. The right shoulder mounting strap 110a further defining an upper curved region that is adapted to rest on the right shoulder 117a of the operator 112 so as to support the first respirator bellow 104a including its weight and to keep it from falling away from the operator 112. Similarly, the left shoulder mounting strap 110b is attached to the second respirator bellow 104b so as to define an opening that receives the left arm 115b there through. The left shoulder mounting strap 110b further defining an upper curved region that is adapted to rest on the left shoulder 117b of the operator 112 so as to support the second respirator bellow 104b including its weight and to keep it from falling away from the operator 112.

As illustrated in FIGS. 1, 2, the respirator bellows 104a, 104b are attached together via the front and rear mounting straps 110c, 110d of the respirator harness 109. In particular, the distal ends of the front mounting strap 110c are attached to the front portions of the respirator bellows 104a, 104b so as to cross adjacent the front side of the torso 114, and the distal ends of the rear mounting strap 110d are attached to the rear portions of the respirator bellows 104a, 104b so as to cross adjacent the rear side of the torso 114. In one embodiment, the mounting straps 110 are configured to be worn by the operator 112 like a vest or jacket that can be secured with a locking device 138, such as a buckle, button, hooked clasp, snap, or hook and loop clasp. For example, the front or rear mounting strap 110c, 110d may be adapted to separate into at least two sections along its length so that the locking device 138 can be used to re-attach the separated sections in a manner similar to that of a belt buckle. As a result, the locking device 138 allows the operator 112 to wear the harness in a manner so as to readily mount and dismount the respirator harness 109 to and from the torso 114.

Additionally, the respirator bellows 104a, 104b may be stitched to the harness 109 including the mounting straps 110a, 110b, 110c, 110d using generally known methods of sewing or stitching such that the first respirator bellow 104a is positioned under the right arm 115a of the operator 112, and the second respirator bellow 104b is positioned under the left arm 115b of the operator 112. In particular, the first respirator bellow 104a may be stitched to the distal ends of the right shoulder mounting strap 110a and the right distal ends of the front and rear mounting straps 110c, 110d as illustrated in FIGS. 1, 2. Likewise, the second respirator bellow 104b may be stitched to the distal ends of the left shoulder mounting strap 110b and the left distal ends of the front and rear mounting straps 110c, 110d.

It should be appreciated by one skilled in the art that the respirator 100 may comprise either the first or second respirator bellow 104a, 104b attached to the respirator harness 109 including one or more of the mounting straps 110a, 110b, 110c, 110d without departing from the scope of the present invention. In this particular embodiment, a single respirator bellow, 104a, 104b, may be used by the operator 112 to deliver air or oxygen to the respirator mask 102 in a manner as previously described.

In one embodiment, the respirator conduits 106a, 106b including the additional respirator conduits 106c, 106d, 106e comprise flexible tubing that can be formed of resilient materials, such as plastic, rubber, etc. As illustrated in FIG. 1, one distal end of the front respirator conduits 106a, 106b are attached to the front portion of the respirator bellows 104a, 104b via output valves 134 in a generally known manner. The other distal end of the front respirator conduits 106a, 106b are attached to the coupler 128 of the respirator mask 102 in a generally known manner. A first respirator conduit 106a is attached between the output valve 134 of the first respirator bellow 104a and the first input port 130a of the coupler 128, and a second respirator conduit 106b is attached between the output valve 134 of the second respirator bellow 104b and the second input port 130b of the coupler 128. Advantageously, this described interconnection provides the respirator mask 102 with air or oxygen from the respirator bellows 104a, 104b via the first and second respirator conduits 106a, 106b.

As illustrated in FIG. 2, additional respirator conduits 106c, 106d may be attached to the rear portion of the respirator bellows 104a, 104b via input valves 136 in a generally known manner. In one embodiment, third, fourth, and fifth respirator conduits 106c, 106d, 106e are attached between the input valves 136 of the respirator bellows 104a, 104b and the air or oxygen supply device 108 via a junction box 140 in a generally known manner. The junction box 140 may be used to split the fifth respirator conduit 106e into two separate respirator conduits 106c, 106d such that the third respirator conduit 106c is attached to the input valve 136 of the first respirator bellow 104a and the fourth respirator conduit 106d is attached to the input valve 136 of the second respirator bellow 104b.

In one embodiment, the air or oxygen supply device 108 may comprise a generally known compressed gas tank that is filled with compressed air or oxygen. The compressed gas tank may comprise a regulator valve 142 that regulates the amount of air or oxygen delivered to the respirator 100. In another embodiment, the air or oxygen supply device may comprise a generally known machine that generates oxygen from the surrounding external air. In still another embodiment, the additional respirator conduits 106c, 106d, 106e may be disconnected from the respirator bellows 104a, 104b such that the input valves 136 draw in air or oxygen from the surrounding external environment. Therefore, the improved respirator 100 may used in situations where the air or oxygen supply device 108 is unavailable or disconnected.

Figure 3A:
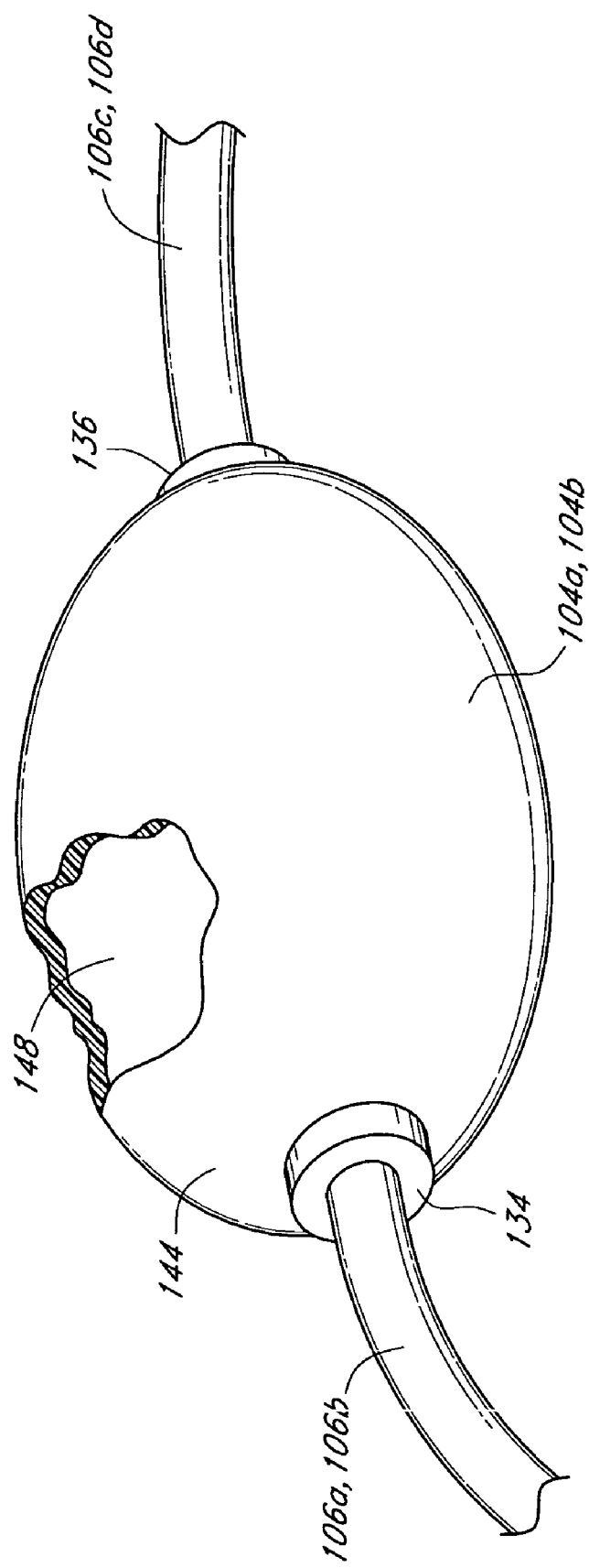
FIG. 3A illustrates one embodiment of the respirator bellows comprising flexibly resilient containers, such as bags or sacks, having an outer skin that is adapted to define an inner closed chamber.

FIG. 3A illustrates one embodiment of the respirator bellows 104a, 104b, wherein the respirator bellows 104a, 104b may comprise flexibly resilient containers, such as bags or sacks, having an outer skin 144 that is adapted to define an inner closed chamber 148. The outer skin 144 is adapted to be substantially gas tight such that gas present within the inner closed chamber 148 is surrounded by the outer skin 144 and has a decreased tendency to escape or leak through the outer skin 144. Therefore, the flexibly resilient material used to form the outer skin 144 may be selected so as to exhibit this desirable characteristic. In one embodiment the outer skin 144 comprises rubber. In various alternative embodiments, the outer skin 144 may comprise alternative types of flexibly resilient materials that are generally known in the art without departing from the scope of the present invention.

As will be described in greater detail herein below with reference to FIGS. 3B, 3C, the respirator bellows 104a, 104b may be compressed or deflated so as to exhaust gas, such as air or oxygen, from within the inner closed chamber 148 or decompressed so as to draw gas into the inner closed chamber 148. In addition, the respirator bellows 104a, 104b may comprise uni-directional output and input valves 134, 136. In one embodiment, the output valves 134 are adapted to allow gas to flow from the inner closed chamber 148, and the input valves 136 allow gas to flow into the inner closed chamber 148.

Figure 3B:
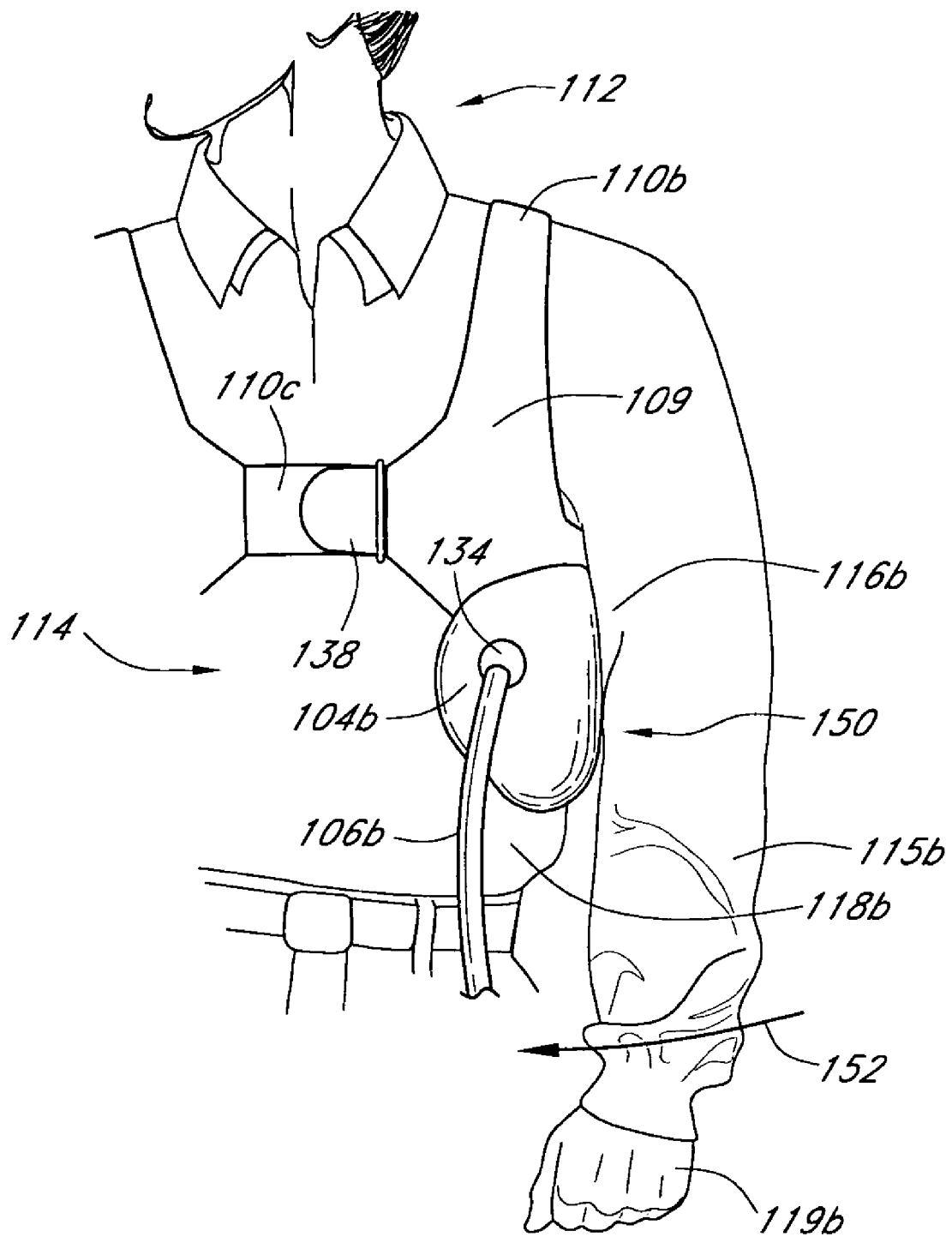
FIG. 3B illustrates one of the respirator bellows in a deflated or compressed configuration.

FIG. 3B illustrates one embodiment of the second respirator bellow 104b in a deflated or compressed configuration 150. FIG. 3C illustrates one embodiment of the second respirator bellow 104b in an inflated or decompressed configuration 154. It should be appreciated by one skilled in the art that the following discussion relating to the scope and functionality of the second respirator bellow 104b may similarly pertain to the first respirator bellow 104a without departing from the scope of the present invention.

During respirator 100 operation, the respirator bellows 104a, 104b function as air or oxygen pumps that are actuated by the operator 112 moving at least one arm 115a, 115b in an adductive motion 152 or abductive motion 156. For example, as illustrated in FIG. 3B, during respirator bellow compression, the adductive motion 152 of the operator's left arm 115b presses the second respirator bellow 104b against or towards the left side portion 118b of the torso 114 of the operator 112 to thereby force air or oxygen that is within the inner closed chamber 148 of the second respirator bellow 104b to flow through the respirator conduits 106a, 106b to the respirator mask 102 via the output valves 134.

Figure 3C:
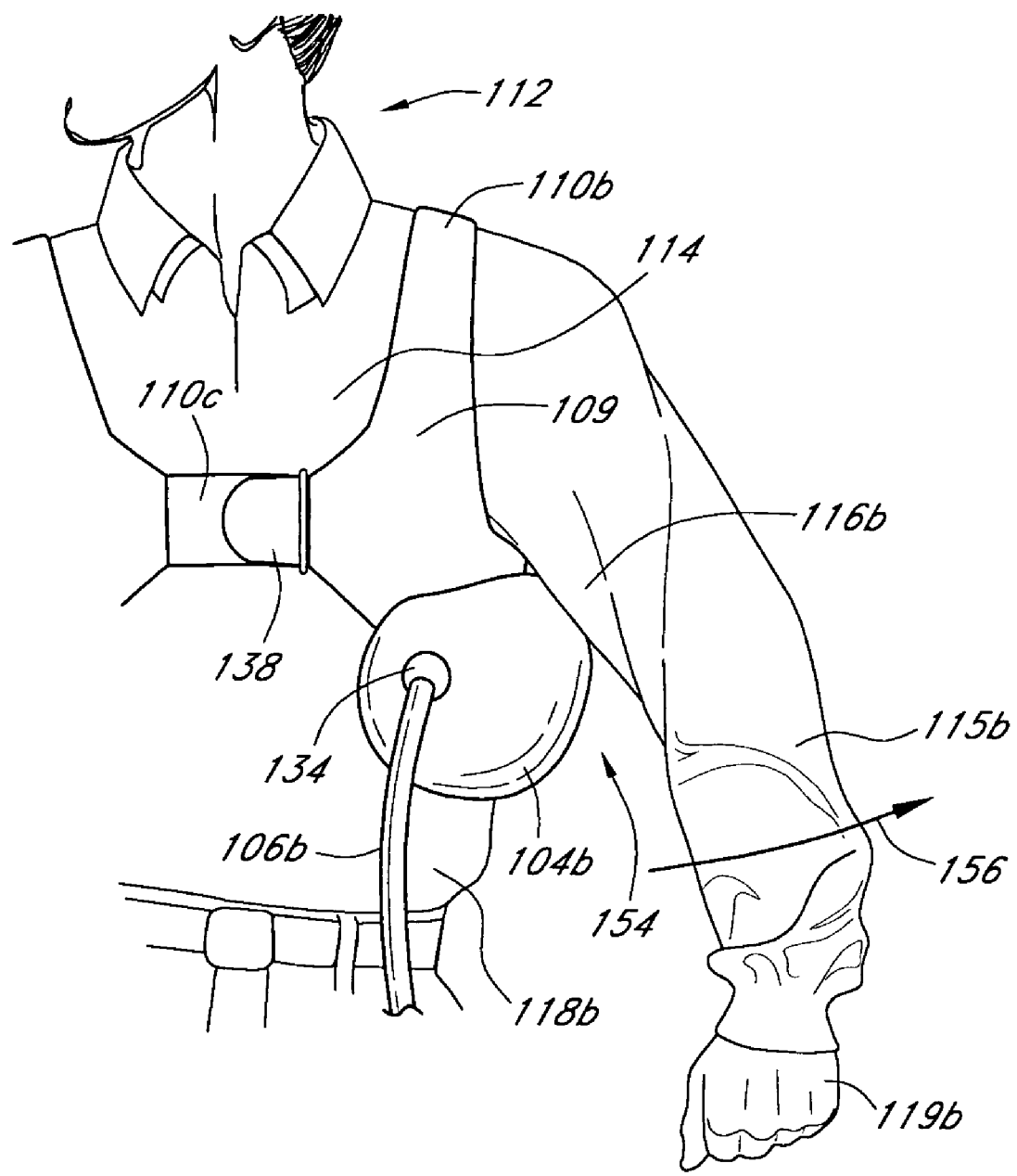
FIG. 3C illustrates one respirator bellows in an inflated or decompressed configuration.

In addition, as illustrated in FIG. 3C, during respirator bellow decompression or release, the abductive motion 156 of the operator's left arm 115b allows the second respirator bellow 104b to resiliently expand away from the left side portion 118b of the torso 114 of the operator 112 to thereby draw in air or oxygen from either the supply device 108 or the surrounding environment into the inner closed chamber 148 of the second respirator bellow 104b via the additional respirator conduits 106d, 106e and the input valve 136. The adductive and abductive motion 152, 156 can be consecutively repeated to mimic a pumping motion. It should be appreciated by one skilled in the art that, during respirator bellow decompression or release, the input valve 136 of the second respirator bellow 104b may be exposed to the surrounding environment so that air or oxygen may be drawn in from the external environment without departing from the scope of the present invention. It should also be appreciated that the previous discussion may be applied to the first respirator bellow 104a in a similar manner without departing from the scope of the present invention.

Advantageously, the actuation of the pumping motion is a hands-free operation, whereby the operator 112 can forcefully deliver air or oxygen to the respirator mask 102 and the patient by consecutively adducting and abducting at least one arm. In addition, the air or oxygen delivery to the respirator mask 102 and patient can be regulated by the operator 112 depending on the speed in which the operator 112 pumps the respirator bellows 104a, 104b with at least one of the arms. Further scope and functionality of the air or oxygen delivery will be described in greater detail herein below.

Figure 4A:
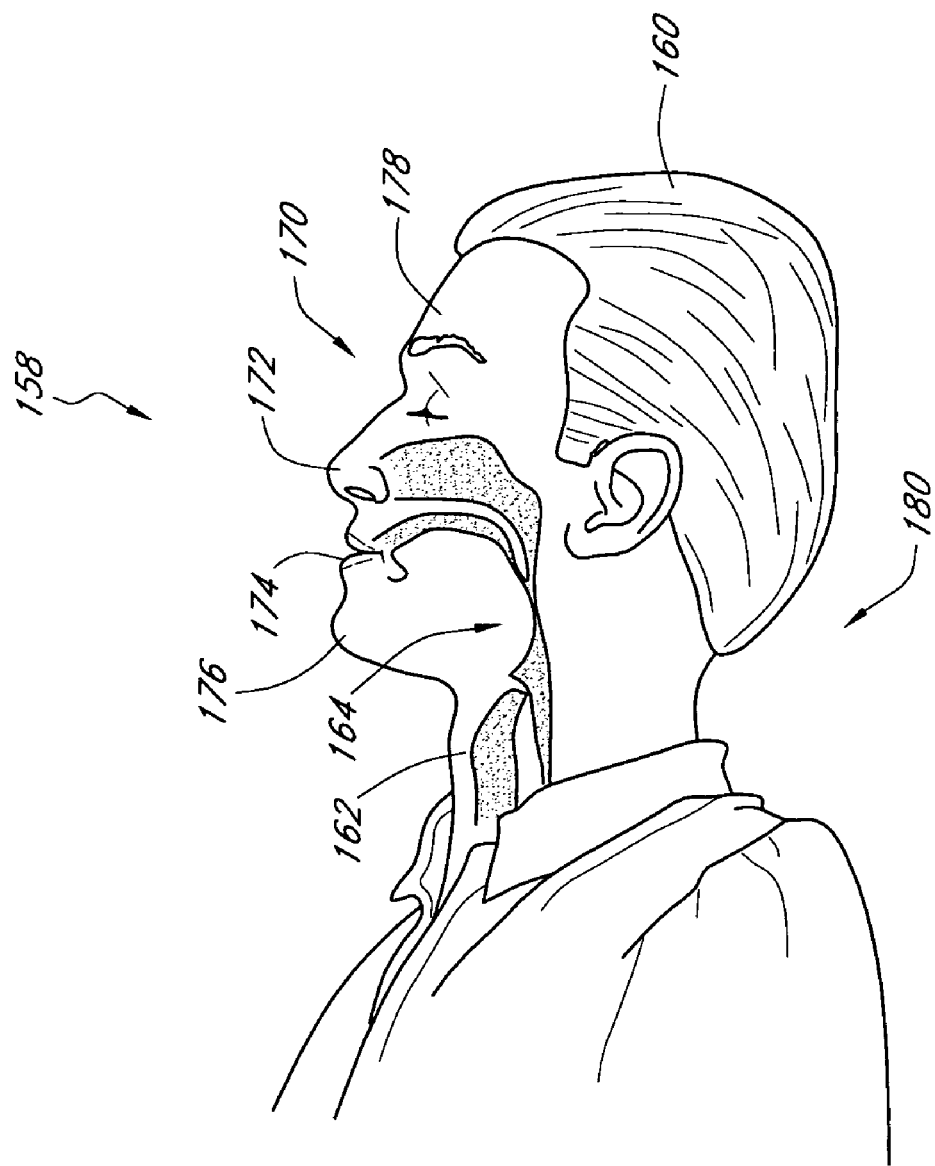
FIG. 4A illustrates one embodiment of a patient having a head and a throat with an occluded airway, wherein the patient is lying face up on a ground surface.

FIG. 4A illustrates one embodiment of a patient 158 having a head 160 and a throat 162 with an occluded airway 164, wherein the patient 158 is lying face up on a ground surface 180. As illustrated, the head 160 of the patient 158 includes a face 170 with a nose 172, a mouth 174, a chin 176, and a forehead 178. As is generally known, the muscle tone of an unresponsive patient, such as the illustrated patient 158, may often be impaired due, for example, to unconsciousness, which may result in the occlusion or obstruction of the airway 164 by soft tissues at the back of the mouth 174 or throat 162, such as the region of the base of the tongue, the epiglottis, the larynx, or the pharynx. Fortunately, occlusion or obstruction relief may be achieved by using a generally known resuscitation technique involving tilting the head 160 and lifting the chin 176 as illustrated in FIG. 4B.

Figure 4B:
FIG. 4B illustrates one embodiment of the patient having the throat of FIG. 4A with an open airway.

FIG. 4B illustrates one embodiment of the patient 158 having the throat 162 of FIG. 4A with an open airway 166. As illustrated, the head 160 of the patient 158 can be tilted backwards by pressing the forehead 178 of the patient 158 towards the ground surface 180 with the left hand 119b of the operator 112, and simultaneously lifting the chin 176 of the patient 158 upwards with the right hand 119a of the operator 112 so as to open the airway 166. As a result of opening the airway 166, the patient 158 can more efficiently receive air or oxygen for resuscitation using the improved respirator 100 as previously described herein.

Figure 4C:
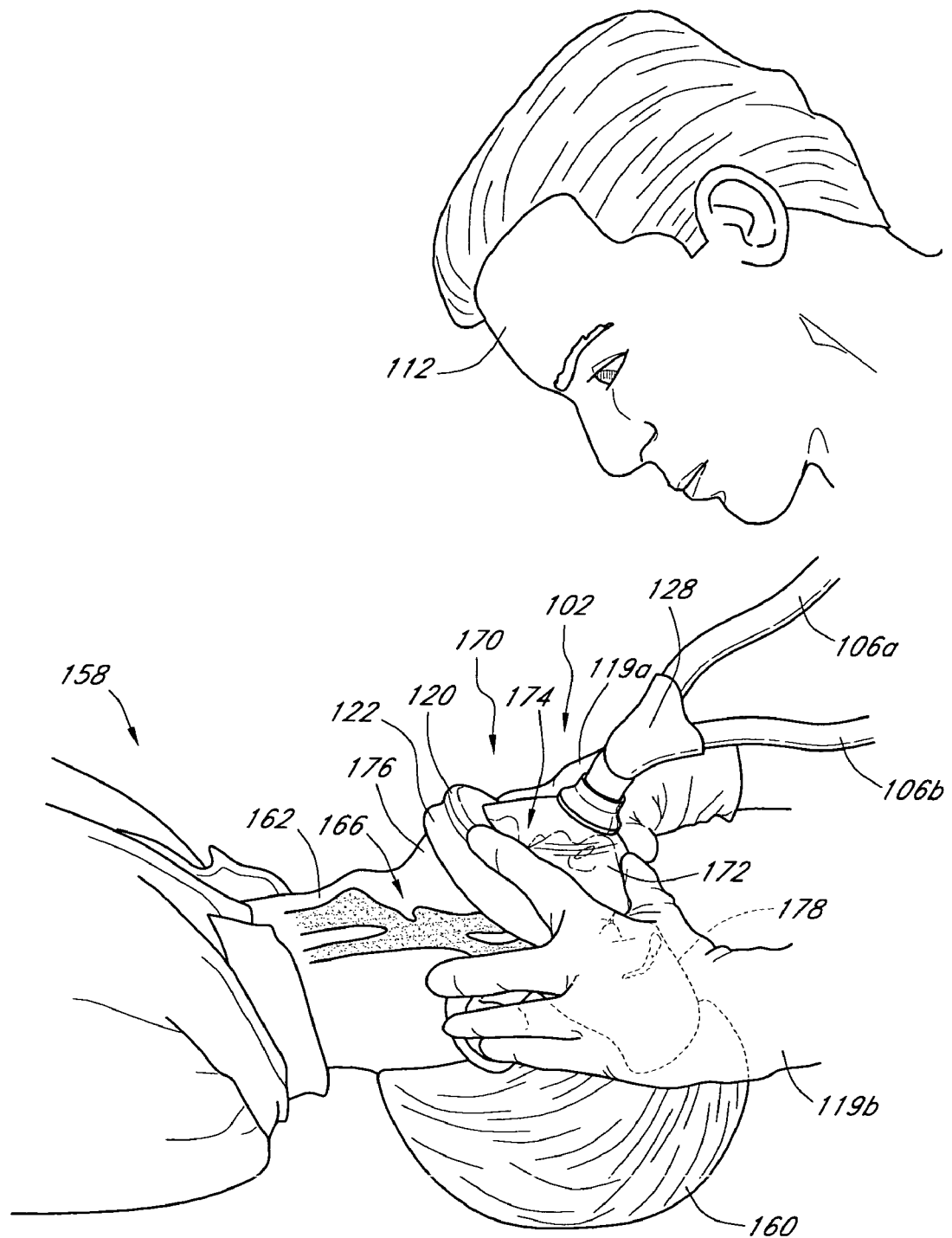
FIG. 4C illustrates one embodiment of the operator utilizing the improved respirator of FIGS. 1–3C on the patient.

FIG. 4C illustrates one embodiment of the operator 112 utilizing the improved respirator 100 of FIGS. 1–3C on the patient 158. The operator 112 is shown leaning over the head 160 of the patient 158, tilting the head 160 of the patient backward with the right and left hands 119a, 119b, and also securing the respirator mask 102 in position with the right and left hands 119a, 119b. As illustrated, the operator 112, for example, can use the first finger and the thumb of each hand 119a, 119b to secure the respirator mask 102 to the face 170 of the patient 158 over the nose and mouth 172, 174 of the patient 158, while using the remaining fingers on the hands 119a, 119b to lift the chin 176 adjacent to the jaw line of the mouth 174. Additionally, the thumbs of each hand 119a, 119b can press down on the respirator mask 102 adjacent the forehead 178 of the patient 158 so as to tilt the head 160 in a manner as previously described with reference to FIG. 4B. Advantageously, this technique effectively secures the respirator mask 102 to the face 170 of the patient 158 and opens the airway 166 of the throat 162. As will be described in greater detail herein below with reference to FIGS. 4D, 4E, the operator 112 can then readily actuate one or more of the respirator bellows 104a, 104b by producing an adductive and abductive motion with at least one arm. To simplify the following discussion, it should be appreciated that FIG. 4C including any of the previous FIGS. 1–4B may be used in conjunction with FIGS. 4D, 4E to illustrate the scope and/or functionality of the present teachings.

Figure 4D:
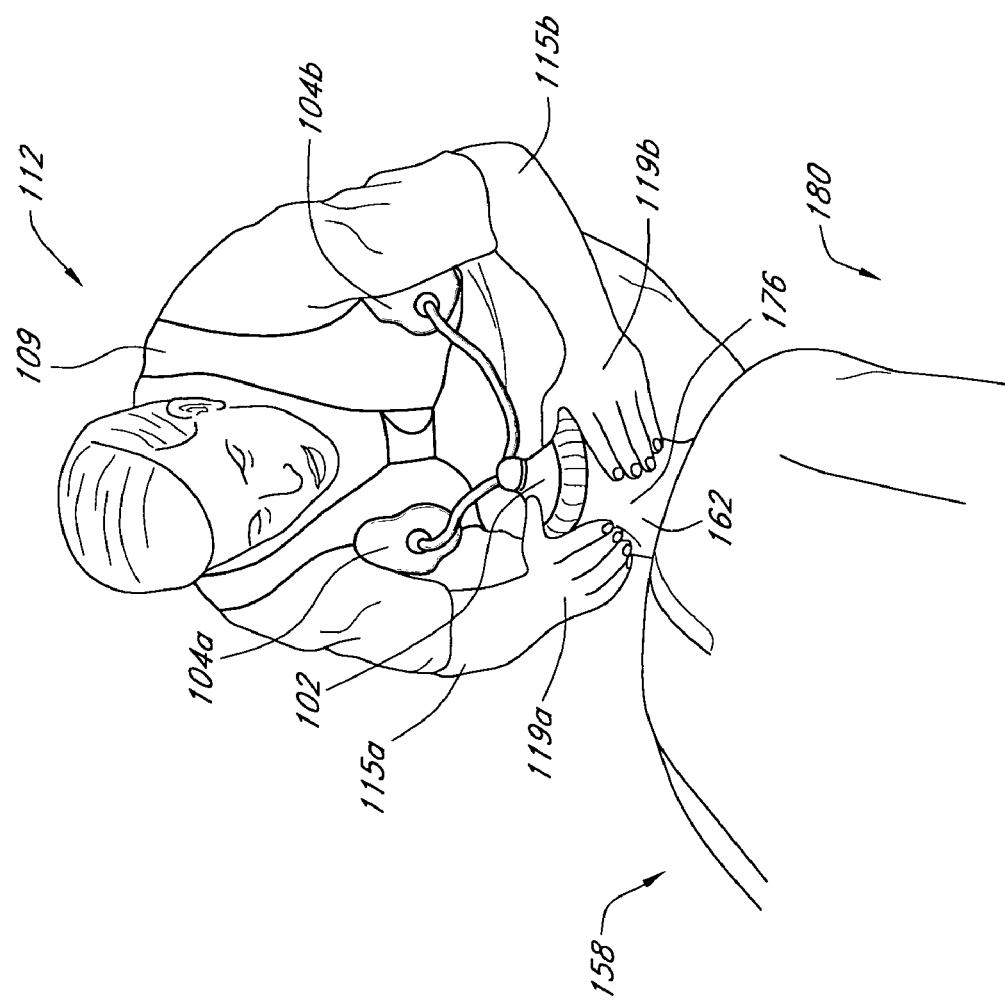
FIG. 4D illustrates one embodiment of a positional orientation of the operator in relation to the patient, when the patient is lying face up on the ground surface.

FIG. 4D illustrates one embodiment of a positional orientation of the operator 112 in relation to the patient 158, when then patient 158 is lying face up on the ground surface 180. In one embodiment, the operator 112 is shown generally positioned adjacent the top of the patient's head 160 so as to be substantially parallel to the patient 158. In a manner as previously described, the operator 112 positions the respirator mask 102 over the patient's face 170 so as to simultaneously cover the patient's nose 172 and mouth 174 with the open-ended cavity 124 of the facial cup 120. In addition, the operator 112 positions right and left hands 119a, 119b on the respirator mask 102 adjacent the coupler 128 and under the patient's chin 176. Then, the operator 112 firmly presses the respirator mask 102 downward to thereby secure the retaining edges 122 of the respirator mask 102 to the face 170 of the patient 158 and lifts the chin 176 of the patient 158 so as to tilt the head 160 of the patient 158 and open the airway 166 in a manner as previously described. Moreover, once the respirator mask 102 is properly secured in position and the patient's head 160 is tilted, the operator 112 may begin pumping one or more of the respirator bellows 104a, 104b so as to deliver air or oxygen to the patient 158 in a manner as previously described with reference to FIGS. 1, 2.

Figure 4E:
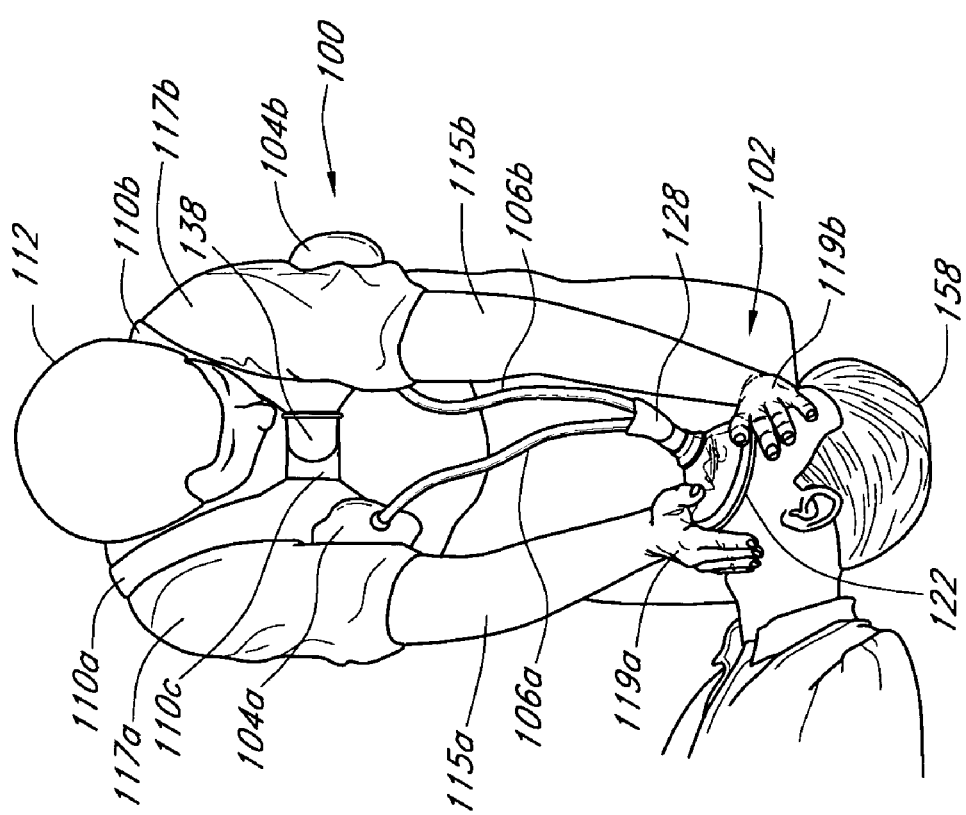
FIG. 4E illustrates an alternative embodiment of securing the respirator mask to the patient's face and tilting the patient's head so as to open the airway.

FIG. 4E illustrates an alternative embodiment of securing the respirator mask 102 to the patient's face 170 and tilting the patient's head 160 so as to open the airway 166. The operator 112 is shown generally positioned adjacent the side of the patient's head 160 so as to be substantially perpendicular to the patient 158. In this particular embodiment, the right hand 119a of the operator 112 is positioned adjacent the patient's chin 176 so that the thumb and first finger of the right hand 119a are used to secure the respirator mask 102 to the patient's face 170 and the remaining fingers on the right hand 119a lift the chin 176 so as to tilt the patient's head 160 in a manner as previously described. In addition, the left hand 119b of the operator 112 is positioned adjacent the forehead 178 of the patient 158 so that the thumb and first finger of the left hand 119b are used to secure the mask to the patient's face 170 and the remaining fingers press against the patient's forehead 176 so as to tilt the patient's head 160 in a manner as previously described.

Advantageously, the improved respirator 100 allows the operator 112 to properly secure the respirator mask 102 in position on the face of the patient 158 with more than one hand 119a, 119b, which results in less air or oxygen leakage around the retaining edges 122 of the facial cup 120. Also, the improved respirator 100 is substantially helpful in situations where an operator 112 with small hands has difficulty securing the respirator mask 102 in position with only one hand 119a or 119b, while trying to tilt the head 160 of the patient 158 so as to open the airway 166 of the patient's throat 162.

Additionally, the improved respirator 100 of the present invention allows a single operator 112 having small hands to properly secure the respirator mask 102 in position on the face 170 of the patient 158 with both right and left hands 119a, 119b, while tilting the patient's head 160 so as to open the airway 166 of the throat 162. Beneficially, since the operator's hands 119a, 119b are free to firmly hold the respirator mask 102 in position as described herein, a more efficient respiration can be administered to the patient 158 such that air or oxygen leakage is less likely to occur when the respirator mask 102 is properly secured in position on the patient's face 170 with more than one hand 119a, 119b and the airway 166 is open due to the added ability of tilting the patient's head 160 while securing the respirator mask 102 to the patient's face 170.

Although the foregoing description has shown, described and pointed out the fundamental novel features of the invention, it will be understood that various omissions, substitutions, and changes in the form of the detail of the apparatus as illustrated, as well as the uses thereof, may be made by those skilled in the art, without departing from the spirit or scope of the present invention. Consequently, the scope of the invention should not be limited to the foregoing discussion, but should be defined by the appended claims.

What is claimed is:

1. A respiration system for providing compressed gas to a patient, the system comprising:
   a mask adapted to cover the patient's nose and mouth;
   a pair of bellows having an inner chamber and an input port and an output port connected thereto, wherein the pair of bellows is compressible by a user such that when being compressed, the one pair of bellows exhausts gas out the inner chamber via the output port and wherein each of the bellows is resiliently expandable such that when the compression has ceased, the pair of bellows expand and draw gas into the inner chamber via the input port;
   at least one gas conduit interconnecting the output port of the pair of bellows to the mask such that compressed gas is conveyed to the patient via the at least one gas conduit and the mask in response to compression of the pair of bellows by the user; and
   a harness attached to the pair of bellows, wherein the harness is sized so as to be worn by the user so that the bellows are maintained by the harness in a position adjacent the user's right and left armpit so that the user can compress either or both of the pair of bellows between the user's inner upper arms and torso thereby freeing the user's hands to hold the mask so as to cover the patient's nose and mouth; and
   wherein the harness comprises a front strap connected between the pair of bellows across the front portion of the user's torso and a rear strap connected between the pair of bellows across the rear portion of the user's torso, and wherein the front strap comprises a locking device that is detachable and reattachable so as to allow the user to remove the harness.

2. The system of claim 1, further comprising a gas source coupled to the input port.

3. The system of claim 2, wherein the gas source comprises a source of compressed oxygen.

4. The system of claim 1, wherein the harness is sized so as to maintain the pair of bellows in a position at a location where the user can compress the pair of bellows between the user's inner upper arm and torso.

5. The system of claim 1, wherein the harness comprises a pair of shoulder straps that rest on the shoulder of the user so as to respectively support the pair of bellows when the at least one bellows is positioned between the inner upper arms and the torso of the user.

6. The respirator of claim 1 wherein the locking device is selected from the group consisting of a hook and loop fastener clasp, a button, a snap, a hook, and a buckle.

7. An air delivery system for a patient administered by an operator comprising:
   a mask adapted to cover at least a portion of the patient's face;
   a harness sized so as to be worn about the torso of the operator;
   a first bellow attached to the harness such that the first bellow is positioned between the operator's right arm and torso when the harness is worn by the operator, the first bellow having a first conduit attached to the mask so as to communicate therewith, wherein the first bellow can be compressed with a downward motion of the operator's right arm towards the operator's torso so as to force gas from the first bellow into the mask via the first conduit, and wherein compression of the first bellow allows the operator to secure the mask to the patient's face with the operator's right hand;
   a second bellow attached to the harness such that the second bellow is positioned between the operator's left arm and torso when the harness is worn by the operator, the second bellow having a second conduit attached to the mask so as to communicate therewith, wherein the second bellow can be compressed with a downward motion of the operator's left arm towards the operator's torso so as to force gas from the second bellow into the mask via the second conduit, and wherein compression of the second bellow allows the operator to secure the mask to the patient's face with the operator's left hand; and
   a harness that is adapted to be secured to the operator's torso, the harness having a right shoulder strap that rests on the operator's right shoulder, a left shoulder strap that rests on the operator's left shoulder, a front strap that crosses the operator's chest, and a rear strap that crosses the operator's back.

8. The system of claim 7, wherein the first and second bellows can be independently or simultaneously compressed.

9. The system of claim 8, wherein the first bellow can be decompressed with an upward motion of the right arm away from the torso of the operator so as to draw gas into the first bellow.

10. The system of claim 9, wherein the second bellow can be decompressed with an upward motion of the left arm away from the torso of the operator so as to draw gas into the second bellow.

11. The system of claim 10, wherein the first and second bellows can be independently or simultaneously decompressed.

12. The system of claim 7, wherein the first bellow is attached to the right shoulder strap of the harness and the second bellow is attached to the left shoulder strap of the harness.

13. The respirator of claim 8, wherein the front strap of the harness comprises a locking device that is detachable and re-attachable so as to allow the operator to wear the harness.

14. The respirator of claim 7, wherein the locking device is selected from the group consisting of a hook and loop fastener clasp, a button, a snap, a hook, and a buckle.

* * * * *

UNITED STATES PATENT AND TRADEMARK OFFICE
CERTIFICATE OF CORRECTION

| | |
|---|---|
| PATENT NO. | : 7,207,328 B1 |
| APPLICATION NO. | : 10/629409 |
| DATED | : April 24, 2007 |
| INVENTOR(S) | : Armin Altemus |

It is certified that error appears in the above-identified patent and that said Letters Patent is hereby corrected as shown below:

At Column 11, Line 20, before "pair", please delete "one".

At Column 12, Line 54, please delete "8" and insert --7-- therefor.

Signed and Sealed this

Thirty-first Day of July, 2007

JON W. DUDAS
*Director of the United States Patent and Trademark Office*